United States Patent [19]
de Juan, Jr.

[11] Patent Number: 5,919,813
[45] Date of Patent: Jul. 6, 1999

[54] USE OF A PROTEIN TYROSINE KINASE PATHWAY INHIBITOR IN THE TREATMENT OF DIABETIC RETINOPATHY

[75] Inventor: Eugene de Juan, Jr., Phoenix, Md.

[73] Assignee: Johns Hopkins University, School of Medicine, Baltimore, Md.

[21] Appl. No.: 09/041,931

[22] Filed: Mar. 13, 1998

[51] Int. Cl.$^6$ .......................... A61K 31/38; A61K 31/35
[52] U.S. Cl. .......................... 514/432; 514/451; 514/453; 514/456; 514/866
[58] Field of Search .................................. 514/432, 451, 514/656, 866, 453

[56] References Cited

U.S. PATENT DOCUMENTS 5,637,703   6/1997   Mazurek et al. ........................ 544/109

FOREIGN PATENT DOCUMENTS

WO 97/30701   8/1997   WIPO .

OTHER PUBLICATIONS

Barnes, "Effect of Genistein on In Vitro and In Vivo Models of Cancer," *J. Nutr.* 125: 777S–783S (1995).
Barnes et al., "Biochemical Targets of the Isoflavone Genistein in Tumor Cell Lines," *PSEBM* 208: 103–108 (1995).
Burke, Jr. "Protein–Tyrosine Kinase Inhibitors," *Drugs of the Future* 17(2): 119–131 (1992).
Coward et al., "Genistein, Daidzein, and Their β–Blycoside Conjugates: Antitumor Isoflavones in Soybean Foods from American and Asian Diets," *J. Agric. Food Chem.* 41: 1961–1967 (1993).
Cunningham et al. "Synthesis and Biological Evaluation of a Series of Flavones Designed as Inhibitors of Protein Tyrosine Kinases," *Anti–Cancer Drug Design* 7: 365–384 (1992).
Filipeanu et al., "Multiple Effects of Tyrosine Kinase Inhibitors on Vascular Smooth Muscle Contraction," *European Journal of Pharmacology* 281(1): 29–35 (1995) (Abstract).
Fotsis et al., "Genistein, A Dietary Ingested Isoflavonoid Inhibits Cell–Proliferation and In–Vitro Angiogenesis," *Journal of Nutrition* 125(3): 790–797 (1995) (Abstract).
Fotsis et al., "Genistein, a Dietary–Derived Inhibitor of In Vitro Angiogenesis," *PNAS USA* 90: 2690–2694 (1993).
Hayashi et al., "Activation of Protein Tyrosine Phosphorylation After Retinal Branch Vein Occlusion in Cats," *Investigative Ophthalmology & Visual Science* 38(2): 372–380 (1997).
Hayashi et al., "Increase of Protein Tyrosine Phosphorylation in Rat Retina After Ischemia–Reperfusion Injury," *Investigative Ophthalmology & Visual Science* 7(11): 2146–2156 (1996).
Hayashi et al., "Genistein, a Protein Tyrosine Kinase Inhibitor, Ameliorates Retinal Degeneration After Ischemia–Reperfusion Injury in Rat," *Investigative Ophthalmology & Visual Science* 38(6): 1193–1202 (1997).

Hayashi et al., "Role of Protein Tyrosine Phosphorylation in Rat Corneal Neovascularization," *Graefe's Arch. Clin. Exp. Ophthalmol.* 235: 460–467 (1997).
Hayashi et al., "Genistein, A Protein Tyrosine Kinase Inhibitor, Ameliorates Retinal Degeneration After Ischemia–Reperfusion Injury in Rat," *Investigative Ophthalmology and Visual Science* 38(4): 489–B400 (1997) (Abstract).
Herman et al., "Soybean Phytoestrogen Intake and Cancer Risk," *J. Nutr.* 125: 757S–770S (1995).
Kennedy, "The Evidence of Soybean Products as Cancer Preventive Agents," *J. Nutr.* 125: 733S–742S (1995).
Kindy, "Inhibition of Tyrosine Phosphorylation Prevents Delayed Neuronal Death Following Cerebral Ischemia," *Journal of Cerebral Blood Flow and Metabolism* 13: 372–377 (1993).
Koroma et al., "Changes Associated With Tyrosine Phosphorylating During Short–Term Hypoxia in Retinal Microvascular Endothelial Cells In Vitro," *Journal of Cellular Biochemistry* 59: 123–132 (1995).
Koroma et al., "Phosphotyrosine Inhibition and Control of Vascular Endothelial Cell Proliferation by Genistein," *Biochemical Pharmacology* 48(4): 809–818 (1994).
Lamartiniere et al., "Neonatal Genistein Chemoprevents Mammary Cancer,"*PSEBM* 208: 120–123 (1995).
Levitzki et al., "Tyrosine Kinase Inhibition: An Approach to Drug Development," *Science* 267: 1782–1790 (1995).
Lu et al., "Effects of Soya Consumption for One Month on Steroid Hormones in Premenopausal Women: Implications for Breast Cancer Risk Reduction," *Cancer Epidemiology, Biomarkers & Prevention* 5: 63–70 (1996).
Moritoki et al., "Possible Involvement of Tyrosine Kinase in the LPS–Promoted Initiation of L–arginine–Induced Relaxation of Rat Aorta Mediated by Induction of $N_\circ$ Synthase," *Life Sciences* 57(11): PL125–130 (1995) (Abstract).
Ohira et al., "Retinal Ischemia and Cell Proliferation in the Rat: The Role of Soluble Mitogens," *Graefe's Arch. Clin. Exp. Ophthalmol.* 228: 195–199 (1990).
Raines et al., "Biology of Atherosclerotic Plaque Formation: Possible Role of Growth Factors in Lesion Development and the Potential Impact of Soy," *Journal of Nutrition* 125(3 Suppl.): 624S–630S (1995) (Abstract).
Steele et al., "Cancer Chemoprevention Agent Development Strategies for Genistein," *J. Nutr.* 125: 713S–716S (1995).

(List continued on next page.)

*Primary Examiner*—Kevin E. Weddington
*Attorney, Agent, or Firm*—Leydig, Voit & Mayer, Ltd.

[57] ABSTRACT

The present invention is directed to a method for the prophylactic and therapeutic treatment of diabetic retinopathy. The method involves the administration of an inhibitor of the protein tyrosine kinase pathway to an animal, such as a mammal, in particular a human, in an amount sufficient to treat the retina for diabetic retinopathy prophylactically or therapeutically. The inhibitor of the protein tyrosine kinase pathway is preferably genistein or an analogue or prodrug thereof or a pharmaceutically acceptable salt of any of the foregoing.

22 Claims, No Drawings

OTHER PUBLICATIONS

Steusloff et al., "Modulation of Ca2+ Sensitivity in Smooth Muscle by Genistein and Protein Tyrosine Phosphorylation," *Archives of Biochemistry & Biophysics* 320(2): 236–242 (1995) (Abstract).

Wilcox et al., "Thrombic Mechanisms in Atherosclerosis: Potential Impact of Soy Proteins," *Journal of Nutrition* 125(3): 631S–638S (1995) (Abstract).

Xiong et al., "Modulation of Ca(2+)–activated K+ Channel Activity by Tyrosine Kinase Inhibitors in Vascular Smooth Muscle Cell," *European Journal of Pharmacology* 290(2): 117–123 (1995) (Abstract).

Chemical Abstracts (81:13392b) 1974 Blaise.

Chemical Abstracts (86:114978f) 1976 Varma et al.

USE OF A PROTEIN TYROSINE KINASE PATHWAY INHIBITOR IN THE TREATMENT OF DIABETIC RETINOPATHY

TECHNICAL FIELD OF THE INVENTION

The present invention relates to a method for the prophylactic and therapeutic treatment of diabetic retinopathy.

BACKGROUND OF THE INVENTION

More than 14 million people in the United States have diabetes. All people with diabetes are at risk of retinal complications. However, people with type I, i.e., insulin-dependent, diabetes, face a greater risk of severe vision loss than people with type II, i.e., non-insulin dependent, diabetes.

Initially, the high blood glucose level in diabetic people causes an increase in growth factors in their eyes. This condition is known as the "pre-diabetic retinopathy stage" and can lead to retinopathy, if not prophylactically treated.

Retinopathy will affect the majority of diabetic people to some extent during their lifetimes (Anonymous, *MMWR* 42(10): 191–195 (1993)). It is the leading cause of blindness in Americans of age 20 to 74 today and is expected to impair vision in approximately one-third of diabetic people in the United States. Each year in the United States, as many as 40,000 new cases of blindness occur among diabetic people (CDC, unpublished data, 1993). Diabetic people are 25 times more likely than the general population to become blind due to retinopathy.

Diabetic retinopathy has two stages—a nonproliferative stage, which typically occurs first, and a proliferative stage. The nonproliferative stage, which is also referred to as "background diabetic retinopathy," is characterized by thickening of the basement membrane, loss of retinal pericytes, microvascular abnormalities, intraretinal microaneurysms, retinal hemorrhages (also known as "dot blot" hemorrhages), retinal edema, in particular diabetic macular edema, capillary closure associated with retinal ischemia or poor retinal perfusion (i.e., poor vessel development) and soft and hard exudates. The proliferative stage, which affects an estimated 700,000 Americans (Chen et al., *J. Miss. State Med. Assoc.* 36(7): 201–208 (1995)), is characterized by neovascularization and fibrovascular growth (i.e., scarring involving glial and fibrous elements) from the retina or optic nerve over the inner surface of the retina or disc or into the vitreous cavity.

The proliferative stage can lead to rubeotic or neovascular glaucoma. Macular edema can occur in either stage and it, along with complications from retinal neovascularization, are the two major retinal problems that cause the diabetes-related vision loss.

While the pathological stages of diabetic retinopathy are well-described, the molecular events underlying diabetic retinopathy are poorly understood. This is due, in part, to the fact that the disease progresses over ten to thirty years, depending on a given individual.

Tight control of glycemia and hypertension and ophthalmic screening of diabetics appears beneficial in preventing the disease. Current treatment consists of regular observation by an ophthalmologist, laser photocoagulation and vitrectomy.

Macular edema threatening or involving the macular center is treated with focal macular photocoagulation. Small (50µ in diameter), mild-intensity laser burns are targeted at areas of leakage in the macula (Murphy, *Amer. Family Physician* 51(4): 785–796 (1995)). If the macular edema persists, retreatment may be necessary.

Patients with severe to very severe nonproliferative retinopathy and patients, who are at high risk for proliferative retinopathy or who already have early or advanced proliferative retinopathy, are treated with scatter or panretinal photocoagulation. Panretinal photocoagulation involves 1,500–2,000 laser burns, which are 500µ in diameter, in the midperipheral and peripheral portion of the retina (Murphy (1995), supra).

The best documented biochemical mechanism for the development of microvascular complications of diabetes is the sorbitol pathway. In the sorbitol pathway, the enzyme aldose reductase catalyzes the conversion of glucose to sorbitol and galactose to galactitol. Aldose reductase has a low substrate affinity for glucose. Accordingly, when glucose concentrations are normal, the pathway is inactive. During hyperglycemia, the sorbitol pathway becomes active. Activation of the sorbitol pathway is important for retinal pericytes, for example, which do not require insulin for glucose penetration. Similarly, retinal capillary cells appear to contain substantial amounts of aldose reductase (Ferris, *Hospital Practice*: 79–89 (May 15, 1993)).

Given the prevalence of diabetic retinopathy, there remains a need for an effective prophylactic and therapeutic treatment of diabetic retinopathy. Accordingly, it is a principal object of the present invention to provide a method of prophylactically and therapeutically treating diabetic retinopathy, including treatment at the pre-diabetic retinopathy stage, the nonproliferative diabetic retinopathy stage, and the proliferative diabetic retinopathy stage. This and other objects of the present invention will become apparent from the detailed description provided herein.

BRIEF SUMMARY OF THE INVENTION

The present invention is directed to a method for the prophylactic and therapeutic treatment of diabetic retinopathy, including treatment at the pre-diabetic retinopathy stage, the nonproliferative diabetic retinopathy stage, and the proliferative diabetic retinopathy stage. The method involves the administration of an inhibitor of the protein tyrosine kinase pathway. Preferably, the inhibitor of the protein tyrosine kinase pathway is a compound of formula:

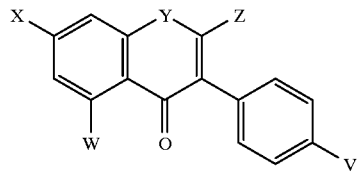

wherein V, W and X are selected from the group consisting of hydro, hydroxyl, alkoxy, halo, an ester, an ether, a carboxylic acid group, a pharmaceutically acceptable salt of a carboxylic acid group, and —SR, in which R is hydrogen or an alkyl group, and Y is selected from the group consisting of oxygen, sulfur, C(OH), and C=O, and Z is selected from the group consisting of hydro and C(O)OR$_1$, wherein R$_1$ is an alkyl. Preferably, the alkoxy is a C$_1$–C$_6$ alkoxy. Preferably, the halo is fluorine, chlorine or bromine. Preferably, the ester is a C$_1$–C$_6$ ester. Preferably, the ether is a C$_1$–C$_6$ ether. Preferred pharmaceutically acceptable salts of the carboxylic acid group include sodium and potassium salts. Preferably, the alkyl groups are C$_1$–C$_6$ alkyl groups. Desirably, the protein tyrosine kinase pathway inhibitor is genistein.

DETAILED DESCRIPTION OF THE INVENTION

The present invention is predicated on the discovery that tyrosine phosphorylation is increased in the early stages of non-ischemic microvascular diabetic retinopathy and that an inhibitor of the protein tyrosine kinase pathway, specifically genistein, is effective in preventing diabetic retinopathy. Accordingly, the present invention provides a method for the prophylactic and therapeutic treatment of diabetic retinopathy, including treatment at the pre-diabetic retinopathy stage, the nonproliferative diabetic retinopathy stage, and the proliferative diabetic retinopathy stage. By "prophylactic" is meant the protection, in whole or in part, against diabetic retinopathy, in particular diabetic macular edema. By "therapeutic" is meant the amelioration of diabetic retinopathy, itself, and the protection, in whole or in part, against further diabetic retinopathy, in particular diabetic macular edema.

The method comprises the administration of an inhibitor of the protein tyrosine kinase pathway in an amount sufficient to treat the retina for retinopathy prophylactically or therapeutically. Any inhibitor of the protein tyrosine kinase pathway can be used in the method of the present invention as long as it is safe and efficacious. Herein, "PTK inhibitor" will be used to refer to such compounds and is intended to encompass all compounds that affect the protein tyrosine kinase pathway at any and all points in the pathway.

Preferably, the PTK inhibitor is genistein (5,7-dihydroxy-3-(4-hydroxyphenyl)-4H-1-benzopyran-4-one) or a pharmaceutically acceptable, protein tyrosine kinase pathway-inhibiting analogue or prodrug thereof or a pharmaceutically acceptable salt of any of the foregoing. Accordingly, the PTK inhibitor can be a compound of the following formula:

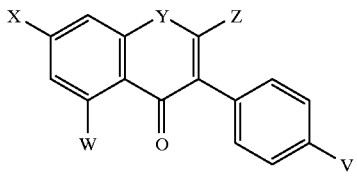

wherein V, W and X are selected from the group consisting of hydro, hydroxyl, alkoxy, halo, an ester, an ether, a carboxylic acid group, a pharmaceutically acceptable salt of a carboxylic acid group, and —SR, in which R is hydrogen or an alkyl group, and Y is selected from the group consisting of oxygen, sulfur, C(OH), and C=O, and Z is selected from the group consisting of hydro and C(O)OR$_1$, wherein R$_1$ is an alkyl. Preferably, the alkoxy is a C$_1$–C$_6$ alkoxy. Preferably, the halo is fluorine, chlorine or bromine. Preferably, the ester is a C$_1$–C$_6$ ester. Preferably, the ether is a C$_1$–C$_6$ ether. Preferred pharmaceutically acceptable salts of the carboxylic acid group include sodium and potassium salts. Preferably, the alkyl groups are C$_1$–C$_6$ alkyl groups. Desirably, the protein tyrosine kinase pathway inhibitor is genistein.

The prodrug can be any pharmaceutically acceptable prodrug of genistein, a protein tyrosine kinase pathway-inhibiting analogue of genistein, or a pharmaceutically acceptable salt of either of the foregoing. One of ordinary skill in the art will appreciate, however, that the prodrug used must be one that can be converted to an active PTK inhibitor in or around the retina. A preferred prodrug is a prodrug that increases the lipid solubility of genistein, a protein tyrosine kinase pathway-inhibiting analogue of genistein, or a pharmaceutically acceptable salt of either of the foregoing. A preferred prodrug is one in which one or more of V, W and X are independently derivatized with an ester, such as pivalic acid.

Compounds of the above formula are widely available commercially. For example, genistein is available from LC Laboratories (Woburn, Mass.). Those compounds that are not commercially available can be readily prepared using organic synthesis methods known in the art.

Whether or not a particular analogue, prodrug or pharmaceutically acceptable salt of a compound in accordance with the present invention can treat retinopathy prophylactically or therapeutically can be determined by its effect in the rat model used in Example 1. Alternatively, analogues, prodrugs and pharmaceutically acceptable salts of inhibitors of the protein tyrosine kinase pathway can be tested by in vitro studies of endothelial cell proliferation and in other models of diabetic retinopathy, such as Streptozotocin.

In addition, color Doppler imaging can be used to evaluate the action of a drug in ocular pathology (Valli et al., *Ophthalmologica* 209(13): 115–121 (1995)). Color Doppler imaging is a recent advance in ultrasonography, allowing simultaneous two-dimension imaging of structures and the evaluation of blood flow. Accordingly, retinopathy can be analyzed using such technology.

The PTK inhibitor can be bound to a suitable matrix, such as a polymeric matrix, if desired, for use in the present inventive method. Any of a wide range of polymers can be used in the context of the present invention provided that, if the polymer-bound compound is to be used in vivo, the polymer is biologically acceptable (see, e.g., U.S. Pat. Nos. 5,384,333 and 5,164,188).

An advantage of genistein is that it is very safe and efficacious. For example, when genistein was orally administered to Zucker diabetic fatty rats, genistein was found to be nontoxic to the retina at dosages ranging from 75 mg/kg/day to 300 mg/kg/day over a period of six months as measured by electroretinography. In addition, oral administration of genistein was found to have no effect on food intake and body weight for male and female rats. Also, no effect of orally administered genistein was found with respect to the weight of the ovaries and the uterus in female rats.

The PTK inhibitor, which is preferably genistein, a protein tyrosine kinase pathway-inhibiting analogue of genistein, a protein tyrosine kinase pathway-inhibiting prodrug of genistein, or a pharmaceutically acceptable salt of any of the foregoing, can be administered in accordance with the present inventive method by any suitable route. Suitable routes of administration include systemic, such as orally or by injection, topical, intraocular, periocular (e.g., subTenon's), subconjunctival, subretinal, suprachoroidal and retrobulbar. The manner in which the PTK inhibitor is administered is dependent, in part, upon whether the treatment of retinopathy is prophylactic or therapeutic. The manner in which the PTK inhibitor is administered for therapeutic treatment of retinopathy is dependent, in part, upon the cause of the retinopathy.

For example, given that diabetes is the leading cause of retinopathy, the PTK inhibitor can be administered prophylactically as soon as the pre-diabetic retinopathy state is detected. For the prophylactic treatment of retinopathy that can result from diabetes, the PTK inhibitor is preferably administered systemically, e.g., orally or by injection. For the therapeutic treatment of nonproliferative diabetic retinopathy, the PTK inhibitor can be administered systemically, e.g., orally or by injection, or intraocularly.

Proliferative diabetic retinopathy can be therapeutically treated by the administration of the PTK inhibitor intraocularly, topically, subconjunctivally or periocularly (e.g., subTenon's), for example. The PTK inhibitor is preferably administered intraocularly, topically, subconjunctivally or periocularly (e.g., subTenon's) for the prophylactic or therapeutic treatment of retinopathy before, during or after surgical removal from an eye of scar tissue generated during neovascularization during the proliferative diabetic stage.

The PTK inhibitor is preferably administered as soon as possible after it has been determined that an animal, such as a mammal, specifically a human, is at risk for retinopathy (prophylactic treatment) or has begun to develop retinopathy (therapeutic treatment). Treatment will depend, in part, upon the particular PTK inhibitor used, the amount of the PTK inhibitor administered, the route of administration, and the cause and extent, if any, of retinopathy realized.

One skilled in the art will appreciate that suitable methods of administering a PTK inhibitor, which is useful in the present inventive method, are available. Although more than one route can be used to administer a particular PTK inhibitor, a particular route can provide a more immediate and more effective reaction than another route. Accordingly, the described routes of administration are merely exemplary and are in no way limiting.

The dose administered to an animal, particularly a human, in accordance with the present invention should be sufficient to effect the desired response in the animal over a reasonable time frame. One skilled in the art will recognize that dosage will depend upon a variety of factors, including the strength of the particular PTK inhibitor employed, the age, species, condition or disease state, and body weight of the animal, as well as the amount of the retina about to be affected or actually affected by retinopathy. The size of the dose also will be determined by the route, timing and frequency of administration as well as the existence, nature, and extent of any adverse side effects that might accompany the administration of a particular PTK inhibitor and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. The present inventive method will typically involve the administration of from about 1 mg/kg/day to about 100 mg/kg/day, preferably from about 15 mg/kg/day to about 50 mg/kg/day, if administered systemically. Intraocular administration typically will involve the administration of from about 0.1 mg total to about 5 mg total, preferably from about 0.5 mg total to about I mg total. A preferred concentration for topical administration is 100 $\mu$M.

Compositions for use in the present inventive method preferably comprise a pharmaceutically acceptable carrier and an amount of a PTK inhibitor sufficient to treat retinopathy prophylactically or therapeutically. The carrier can be any of those conventionally used and is limited only by chemico-physical considerations, such as solubility and lack of reactivity with the compound, and by the route of administration. It will be appreciated by one of ordinary skill in the art that, in addition to the following described pharmaceutical compositions, the PTK inhibitor can be formulated as polymeric compositions, inclusion complexes, such as cyclodextrin inclusion complexes, liposomes, microspheres, microcapsules and the like (see, e.g., U.S. Pat. Nos. 4,997,652, 5,185,152 and 5,718,922).

The PTK inhibitor can be formulated as a pharmaceutically acceptable acid addition salt. Examples of pharmaceutically acceptable acid addition salts for use in the pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable excipients described herein, for example, vehicles, adjuvants, carriers or diluents, are well-known to those who are skilled in the art and are readily available to the public. It is preferred that the pharmaceutically acceptable carrier be one which is chemically inert to the PTK inhibitor and one which has no detrimental side effects or toxicity under the conditions of use.

The choice of excipient will be determined in part by the particular PTK inhibitor, as well as by the particular method used to administer the composition. Accordingly, there is a wide variety of suitable formulations of the pharmaceutical composition of the present invention. The following formulations are merely exemplary and are in no way limiting.

Injectable formulations are among those that are preferred in accordance with the present inventive method. The requirements for effective pharmaceutically carriers for injectable compositions are well-known to those of ordinary skill in the art (see *Pharmaceutics and Pharmacy Practice,* J. B. Lippincott Co., Philadelphia, Pa., Banker and Chalmers, eds., pages 238–250 (1982), and *ASHP Handbook on Injectable Drugs,* Toissel, 4th ed., pages 622–630 (1986)). It is preferred that such injectable compositions be administered intramuscularly, intravenously, or intraperitoneally.

Topical formulations are well-known to those of skill in the art. Such formulations are suitable in the context of the present invention for application to the skin. The use of patches, corneal shields (see, e.g., U.S. Pat. No. 5,185,152), and ophthalmic solutions (see, e.g., U.S. Pat. No. 5,710,182) and ointments, e.g., eye drops, is also within the skill in the art.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inhibitor can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants. Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metals, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-p-aminopropionates, and 2-alkylimidazoline quaternary ammonium salts, and (e) mixtures thereof.

The parenteral formulations will typically contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17.

The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Such compositions can be formulated as intraocular formulations, sustained-release formulations or devices (see, e.g., U.S. Pat. No. 5,378,475). For example, gelantin, chondroitin sulfate, a polyphosphoester, such as bis-2-hydroxyethyl-terephthalate (BHET), or a polylactic-glycolic acid (in various proportions) can be used to formulate sustained-release formulations. Implants (see, e.g., U.S. Pat. Nos. 5,443,505, 4,853,224 and 4,997,652), devices (see, e.g., U.S. Pat. Nos. 5,554,187, 4,863,457, 5,098,443 and 5,725,493), such as an implantable device, e.g., a mechanical reservoir, an intraocular device or an extraocular device with an intraocular conduit (e.g., 100$\mu$-1 mm in diameter), or an implant or a device comprised of a polymeric composition as described above, can be used.

The present inventive method also can involve the co-administration of other pharmaceutically active compounds. By "co-administration" is meant administration before, concurrently with, e.g., in combination with the PTK inhibitor in the same formulation or in separate formulations, or after administration of a PTK inhibitor as described above. For example, corticosteroids, e.g., prednisone, methylprednisolone, dexamethasone, or triamcinalone acetinide, or noncorticosteroid anti-inflammatory compounds, such as ibuprofen or flubiproben, can be co-administered. Similarly, vitamins and minerals, e.g., zinc, anti-oxidants, e.g., carotenoids (such as a xanthophyll carotenoid like zeaxanthin or lutein), and micronutrients can be co-administered. In addition, other types of inhibitors of the protein tyrosine kinase pathway, which include natural protein tyrosine kinase inhibitors like quercetin, lavendustin A, erbstatin and herbimycin A, and synthetic protein tyrosine kinase inhibitors like tyrphostins (e.g., AG490, AG17, AG213 (RG50864), AG18, AG82, AG494, AG825, AG879, AG1112, AG1296, AG1478, AG126, RG13022, RG14620 and AG555), dihydroxy- and dimethoxybenzylidene malononitrile, analogs of lavendustin A (e.g., AG814 and AG957), quinazolines (e.g., AG1478), 4,5-dianilinophthalimides, and thiazolidinediones, can be co-administered with genistein or an analogue, prodrug or pharmaceutically acceptable salt thereof (see Levitzki et al., *Science* 267: 1782–1788 (1995), and Cunningham et al., *Anti-Cancer DrugDesign* 7: 365–384 (1992)). In this regard, potentially useful derivatives of genistein include those set forth in Mazurek et al., U.S. Pat. No. 5,637,703. Neutralizing proteins to growth factors, such as a monoclonal antibody that is specific for a given growth factor, e.g., VEGF (for an example, see Aiello et al., *PNAS USA* 92: 10457–10461 (1995)), or phosphotyrosine (Dhar et al., *Mol. Pharmacol* 37: 519–525 (1990)), can be co-administered. Other various compounds that can be co-administered include inhibitors of protein kinase C (see, e.g., U.S. Pat. Nos. 5,719,175 and 5,710,145), cytokine modulators, an endothelial cell-specific inhibitor of proliferation, e.g., thrombospondins, an endothelial cell-specific inhibitory growth factor, e.g., TNF$\alpha$, an anti-proliferative peptide, e.g., SPARC and prolferin-like peptides, a glutamate receptor antagonist, aminoguanidine, an angiotensin-converting enzyme inhibitor, e.g., angiotensin II, calcium channel blockers, $\psi$-tectorigenin, ST638, somatostatin analogues, e.g., SMS 201–995, monosialoganglioside GM1, ticlopidine, neurotrophic growth factors, methyl-2,5-dihydroxycinnamate, an angiogenesis inhibitor, e.g., recombinant EPO, a sulphonylurea oral hypoglycemic agent, e.g., gliclazide (non-insulin-dependent diabetes), ST638 (Asahi et al., *FEBS Letter* 309: 10–14 (1992)), thalidomide, nicardipine hydrochloride, aspirin, piceatannol, staurosporine, adriamycin, epiderstatin, (+)-aeroplysinin-1, phenazocine, halomethyl ketones, anti-lipidemic agents, e.g., etofibrate, chlorpromazine and spinghosines, aldose reductase inhibitors, such as tolrestat, SPR-210, sorbinil or oxygen, and retinoic acid and analogues thereof (Burke et al., *Drugs of the Future* 17(2): 119–131 (1992); and Tomlinson et al., *Pharmac. Ther.* 54: 151–194 (1992)). Selenoindoles (2-thioindoles) and related disulfide selenides, such as those described in Dobrusin et al., U.S. Pat. No. 5,464,961, are useful protein tyrosine kinase inhibitors. Those patients that exhibit systemic fluid retention, such as that due to cardiovascular or renal disease and severe systemic hypertension, can be additionally treated with diuresis, dialysis, cardiac drugs and antihypertensive agents.

EXAMPLE

The following example further illustrates the present invention but, of course, should not be construed as in any way limiting its scope.

Example 1

This example demonstrates that tyrosine phosphorylation is increased in the early stages of non-ischemic microvascular diabetic retinopathy and that genistein inhibits such tyrosine phosphorylation.

Six pair of litter mates of Zucker rats, i.e., six male retired breeder Zucker diabetic fatty (ZDF, fa/fa) rats and six male retired breeder lean Zucker (fa/+) rats, were obtained (Genetic Models, Inc., Indianapolis, Ind.). The Zucker diabetic fatty rat develops a microvascular retinopathy involving basement membrane thickening of retinal capillaries, pericyte loss, capillary hypercellularity, and increased endothelial intercellular junctions (Danis et al., *Invest. Ophihalmol. Vis. Sci.* 34: 2367–2371 (1993), and Dosso et al., *Diahetologia* 33: 137–144 (1990)). The microvascular changes known to occur in the Zucker diabetic fatty rats are associated with the elevated levels of VEGF and platelet-derived growth factor (PDGF) and with activation of PTK pathways, especially pathways that include phosphatidylinositol-3 kinase (PI3-K) and mitogen-activated protein kinase (MAPK). Each pair of litter mates was between six and seven months of age. Rats were fed with a diet of Purina 5008 rat chow. The animals were treated in accordance with The Association for Research in Vision and Ophthalmology (ARVO) Statement for the Use of Animals in Ophthalmic and Vision Research. The average blood glucose value was more than 500 mg/dl for the Zucker diabetic fatty rats and 120 mg/dl for the control lean rats as measured by glucose oxidase assay at the time of death (Danis et al. (1993), supra).

After an intraperitoneal injection of ketamine (40 mg/kg) and xylazine (4 mg/kg), genistein (LC Laboratories, Woburn, Mass.), which was dissolved in DMSO at the concentration of 10 mg/ml, was injected intraperitoneally into the Zucker diabetic fatty rat and lean rat (non-treated group) at a dose of 50 mg/kg body weight. After two hours, the injection was repeated.

Twenty four hours later, the animals were sacrificed by an injection of intracardiac pentobarbital. Then, 1 mM sodium orthovanadate was injected into the rat eye to inhibit phosphatase activity, the eye was enucleated and the anterior segment was cut away. The vitreous was removed with forceps and the retina was peeled away from the retinal pigmented epithelium/choroid and cut from the optic nerve. The retinal tissue was placed into a tube with 125 $\mu$l of ice-cold lysis buffer (150 mM NaCl, 1% Triton X-100, 0.5% sodium deoxycholate, 0.1% SDS, 50 mM Tris, 100 $\mu$g/ml phenylmethylsulfonyl fluoride (PMSF), 0.3 $\mu$g/ml EDTA, 0.7 $\mu$g/ml pepstatin A, 0.5 $\mu$g/ml leupeptin, 1 mM sodium orthovanadate, and 50 $\mu$M sodium fluoride. The retinal tissue was homogenized with a glass homogenizer and then equal amounts of 2× SDS sample buffer (160 mM Tris-HCl, pH 6.8, 4% SDS, 30% glycerol, 5 B $\beta$-mcercaptoethanol, 10 mM dithiothreitol, 0.01% bromophenol blue) were added. The retinal homogenate was boiled at 95° C. for 5 min and centrifuged at 13,000 rpm for 10 min. The supernatants were collected and stored at −80° C. These total retinal samples were used for gel electrophoresis and Western immunoblot analysis.

Protein concentrations were measured by the Pierce BCA method. Total protein profiles revealed that the Zucker diabetic fatty rat retina had a more strongly stained band at 67 kDa as compared with the lean controls. Treatment with genistein reduced the amount of staining of the 67 kDa band in the Zucker diabetic fatty rat. Other bands in the total protein profiles appeared to be unchanged irrespective of the treatment with genistein.

Anti-phosphotyrosine antibody (PY 20; 1:500 dilution, Transduction Laboratories, Lexington, Ky.), anti-PCNA antibody (1:200 dilution), anti-mitogen-activated protein kinase antibody ( 1:100 dilution, Santa Cruz Biotechnology, Inc., Santa Cruz, Calif.), anti-phosphatidylinositol 3-kinase antibody (1:500 dilution; Upstate Biotechnology, Inc., Lake Placid, N.Y.) were used as primary antibodies in the Western immunoblot analysis. Horseradish peroxidase (HRP) conjugated goat anti-mouse IgG antibody or anti-rabbit IgG antibody (Bio-Rad Laboratories, Inc., Hercules, Calif.) was used as the secondary antibody. Avidin-HRP (Bio-Rad) was used to detect biotinylated molecular markers.

The retinal tissue samples were added to immunoprecipitation buffer (1% Triton X-100, 150 mM NaCl, 10 mM Tris, pH 7.4, 1 mM EGTA, 0.2 mM sodium vanadate, 0.2 mM PMSF, 0.5% NP-40) and homogenized. The supernatant was obtained after centrifugation at 8,000 rpm for 10 min at 4° C. Protein concentrations were measured by the Pierce BCA method. Then 20 $\mu$g of agarose-conjugated phosphotyrosine antibody (PY 20; Transduction Laboratories) were added to each milligram of retinal hmogenate. Retinal homogenates were incubated with the agarose-conjugated phosphotyrosine antibody at 4° C. overnight with shaking. The pellets were collected by centrifugation (10 min at 8,000 rpm) and rinsed with the lysis buffer three times. The pellets were resuspended in 150 $\mu$l of 1X SDS sample buffer per milligram of retinal homogenate and boiled at 95° C. for 5 min. These immunoprecipitated samples were used for gel electrophoresis.

Equal protein amounts of retinal samples were electrophoresed at a constant 200 V for 35 min on 4–20 % gradient minigels (Bio-Rad), using a Bio-Rad Protean II apparatus. Broad range, biotinylated (6.5–200 kDa) and prestained (18.5–106 kDa) molecular weight protein markers (Bio-Rad) were run simultaneously with the samples. After electrophoresis, gels were processed either for total protein staining with Coomassie brilliant blue dye or for Western immunoblot analysis.

After gel electrophoresis, the gels were fixed in 45% methanol and 10% acetic acid aqueous solution for 30 min. Then, they were soaked in saturated picric acid solution briefly and stained with 0.25% aqueous Coomassie brilliant blue (R-250) for a minimum of 2 hr. The gels were destained in 10% acetic acid solution. The procedure was repeated three times.

For Western immunoblot analysis, the gels were electroblotted onto nitrocellulose membranes (Coster Scientific Corp. Cambridge, Mass.) using a trans-blot SD apparatus (Bio-Rad). The membranes for detection of tyrosine-phosphorylated proteins were incubated with 3% bovine serum albumin in Tris-bufered saline (TBS; 20 mM Tris and 150 mM NaCl, pH 7.5) for 1 hr at room temperature. The membranes for detection of other proteins were incubated with 2% of nonfat dried milk (Bio-Rad) in TBS for 1 hr at room temperature. Then, each membrane was incubated with the primary antibody solution overnight at 4° C. Then, the membranes were rinsed with TBS and incubated with HRP-conjugated rat anti-mouse IgG (Jackson Immunoresearch Laboratories, Inc., West Grove, Pa.) or anti-rabbit IgG antibody (Bio-Rad; 1:1,000 dilution) and avidin-HRP (Bio-Rad; 1:10,000 dilution) for 2 hr at room temperature. Following a final rinse series with TBS containing 0.2% Tween-20 15 and TBS alone, the membranes were reacted with enhanced chemiluminescence (ECL) immunodetection reagents (Amersham Life Science Inc., Arlington Heights, Ill.) and exposed to X-ray film. Each Western immunoblot analysis was repeated at least three times.

Overall, the tyrosine phosphorylated proteins in the diabetic retina were increased in comparison to the lean controls at 50, 66, 97 and 116 kDa. Genistein treated diabetic rats showed decreased staining at each molecular weight as compared with the non-treated group.

Western immunoblot analysis of immunoprecipitated tyrosine phosphorylated proteins revealed the increased tyrosine phosphorylation of P13-K at 85 kDa in the diabetic rats as compared to the lean controls. The tyrosine phosphorylated P13-K stained band was reduced after treatment with genistein, especially in the diabetic rat.

Tyrosine phosphorylated MAPK at 44 kDa was increased in the diabetic rats as compared with the lean controls. Similar to P13-K, the level of MAPK in the treated group was also decreased as compared with the non-treated animals group.

Two pairs of rats were used for immunohistochemical analysis of PCNA in the retina. Under deep anesthesia with ketamine and xylazine, the four rats were perfused transcardially with 0.1 M phosphate-buffered saline (PBS; pH 7.4) containing 1 mM orthovanadate, followed by perfusion of 2% paraformaldehyde in 0.1 M PBS for fixation. The eyes were then removed and immersed in the same fixative for 30 min. The anterior segments were removed and the posterior segments were transferred into a graded sucrose solution from 5% to 15% for 2 hrs and incubated in 20% sucrose solution overnight at 4° C. After cryoprotection, the eyes were molded in O.C.T. compound (Miles, Inc., Elkhart, Ind.) and frozen in isopentane with dry ice. The posterior segments were cut into 8 μm sections.

The sections were treated with 3% peroxide to block intrinsic peroxidase, and incubated with 2% normal horse serum for 20 min. After rinsing in 0.1 M PBS three times, the sections were incubated overnight at 4° C. with anti-PCNA antibody (1:1,000 dilution). After the incubation, the sections were rinsed in 0.1 M PBS, and incubated with biotinylated anti-mouse IgG antibody (Vector Laboratories, Inc., Burlingame, Calif.; 1:500 dilution) for 30 min at room temperature, and then incubated with peroxidase-labeled streptavidin (Kirkegaad & Perry Laboratories, Inc., Gaithersburg, Md.; 1:500 dilution). Slides were treated with 3-amino-9-ethylcarbazole (AEC) solution (Sigma Chemical Co., St. Louis, Mo.) to enable visualization. Each set of slides was examined at the same time and three different sets were studies. After mounting with glycerin jelly (7% gelatin, 54% glycerine, 0.7% phenol), photomicrographs were taken with Nomarski optics (Carl Zeiss, Thornwood, N.Y.).

In the Zucker diabetic fatty rat retina, the level of PCNA at 36 kIDa was increased as compared with the lean rats. Genistein reduced this increase as compared to the non-treated group, although not down to the lean control level.

An intense positive immunoreaction in the nuclei of the cells in the nerve fiber and the inner and outer nuclear layers was observed in the Zucker diabetic fatty rats when compared with the lean controls. However, in the genistein treated diabetic rats, fewer immunopositive cells were detected. Incubation of the diabetic rat retina with non-immune mouse IgG, instead of anti-PCNA antibody, showed no immunoreaction.

The above results show that genistein reduced increased levels of phosphotyrosine overall and reduced increased levels of phosphorylated P13-K, MAPK and PCNA (which is indicative of the cells being primed for replication) in the diabetic rat retina. These results suggest that genistein can inhibit the activation of PTK pathways in the retina of diabetic animals with pre-visual changes such that diabetic retinopathy can be prevented.

All of the references cited herein, including patents, patent applications, literature publications, and the like, are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A method of prophylactically or therapeutically treating an animal for diabetic retinopathy, which method comprises administering to said animal an inhibitor of the protein tyrosine kinase pathway in an amount sufficient to treat said animal for diabetic retinopathy prophylactically or therapeutically.

2. The method of claim 1, wherein said inhibitor of the protein tyrosine kinase pathway is a compound of formula:

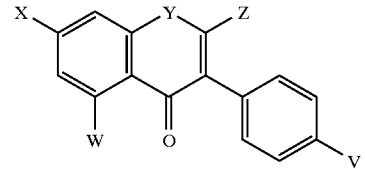

wherein V, W and X are selected from the group consisting of hydro, alkoxy, hydroxyl, halo, an ester, an ether, a carboxylic acid group, a pharmaceutically acceptable salt of a carboxylic acid group, and -SR, in which R is hydrogen or an alkyl group, and Y is selected from the group consisting of oxygen, sulfur, C(OH), and C=O, and Z is selected from the group consisting of hydro and C(O)OR$_1$, wherein R$_1$ is an alkyl, or a protein tyrosine kinase-inhibiting prodrug or pharmaceutically acceptable salt thereof.

3. The method of claim 2, wherein the halo group is selected from the group consisting of fluorine, chlorine and bromine.

4. The method of claim 2, wherein the ester is a $C_1$–$C_6$ ester.

5. The method of claim 2, wherein the ether is a $C_1$–$C_6$ ether.

6. The method of claim 2, wherein said pharmaceutically acceptable salt of a carboxylic acid group is a sodium salt or a potassium salt.

7. The method of claim 2, wherein the alkyl groups are $C_1$–$C_6$ alkyl groups and the alkoxy group is a $C_1$–$C_6$ alkoxy group.

8. The method of claim 2, wherein said inhibitor of the protein tyrosine kinase pathway is genistein.

9. The method of claim 8, wherein genistein is administered systemically.

10. The method of claim 9, wherein genistein is administered in an amount from about 1 mg/kg/day to about 100 mg/kg/day.

11. The method of claim 10, wherein genistein is administered in an amount from about 15 mg/kg/day to about 50 mg/kg/day.

12. The method of claim 9, wherein genistein is administered orally or by injection.

13. The method of claim 9, wherein genistein is administered at the pre-diabetic retinopathy stage.

14. The method of claim 9, wherein genistein is administered at the nonproliferative diabetic retinopathy stage.

15. The method of claim 14, wherein genistein is administered topically, subconjunctivally, retrobulbarly, periocularly, subretinally, suprachoroidally, or intraocularly.

16. The method of claim 14, wherein the administration of genistein prevents diabetic macular edema.

17. The method of claim 14, wherein the administration of genistein treats diabetic macular edema.

18. The method of claim 9, wherein genistein is administered at the proliferative diabetic stage.

19. The method of claim 8, wherein genistein is administered topically, subconjunctivally, retrobulbarly, periocularly, subretinally, suprachoroidally, or intraocularly.

20. The method of claim 19, wherein genistein is administered intraocularly in an amount from about 0.1 mg total to about 5 mg total.

21. The method of claim 20, wherein genistein is administered intraocularly in an amount from about 0.5 mg total to about 1 mg total.

22. The method of claim 18, wherein genistein is administered before, during or after surgical removal from an eye of scar tissue generated during neovascularization during the proliferative diabetic stage.

* * * * *

(12) REEXAMINATION CERTIFICATE (4527th)
United States Patent
de Juan, Jr.

(10) Number: US 5,919,813 C1
(45) Certificate Issued: Jan. 29, 2002

(54) USE OF A PROTEIN TYROSINE KINASE PATHWAY INHIBITOR IN THE TREATMENT OF DIABETIC RETINOPATHY

(75) Inventor: Eugene de Juan, Jr., Phoenix, MD (US)

(73) Assignee: Johns Hopkins University, School of Medicine, Baltimore, MD (US)

Reexamination Request:
No. 90/005,617, Jan. 20, 2000

Reexamination Certificate for:
Patent No.: 5,919,813
Issued: Jul. 6, 1999
Appl. No.: 09/041,931
Filed: Mar. 13, 1998

(51) Int. Cl.⁷ .................. A61K 31/38; A61K 31/35
(52) U.S. Cl. .................. 514/432; 514/451; 514/453; 514/456; 514/866
(58) Field of Search ........................... 514/432

(56) References Cited

U.S. PATENT DOCUMENTS 5,593,997 A  1/1997 Dow et al. ............... 514/258
5,710,173 A  1/1998 Tang et al. ............... 514/447

OTHER PUBLICATIONS

Imai, "Herbimycin A, A Specific Inhibitor of Protein Tyrosine Kinase, in the Treatment of Experimental Proliferative Vitreoretinopathy," *Investigative Ophthalmology & Visual Science*, 36(4), abstract no. 3457–444, S748 (1995).

*Primary Examiner*—Kevin E. Weddington

(57) ABSTRACT

The present invention is directed to a method for the prophylactic and therapeutic treatment of diabetic retionopathy. The method involves the administration of an inhibitor of the protein tyrosine kinase pathway to an animal, such as a mammal, in particular a human, in an amount sufficient to treat the retina for diabetic retinopathy prophylactically or therapeutically. The inhibitor of the protein tyrosine kinase pathway is preferably genistein or an analogue or prodrug thereof or a pharmaceutically acceptable salt of any of the foregoing.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claims 1 and 3–8 are determined to be patentable as amended.

Claims 9–22 dependent on an amended claim, are determined to be patentable.

1. A method of prophylactically or therapeutically treating an animal for diabetic retinopathy, which method comprises administering to said animal an inhibitor of the protein tyrosine kinase pathway, *wherein said inhibitor is a compound of formula:*

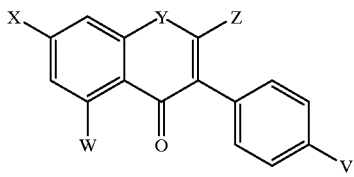

*wherein V, W and X are selected from the group consisting of hydro, alkoxy, hydroxyl, halo, an ester, an ether, a carboxylic acid group, a pharmaceutically acceptable salt of a carboxylic acid group, and —SR, in which R is hydrogen or an alkyl group, and Y is selected from the group consisting of oxygen, sulfur, C(OH), and C=O, and Z is selected from the group consisting of hydro and $C(O)OR_1$, wherein $R_1$ is an alkyl, or a protein tyrosine kinase-inhibiting prodrug or pharmaceutically acceptable salt thereof,* in an amount sufficient to treat said animal for diabetic retinopathy prophylactically or therapeutically.

3. The method of claim [2] *1*, wherein the halo group is selected from the group consisting of fluorine, chlorine and bromine.

4. The method of claim [2] *1*, wherein the ester is a $C_1$–$C_6$ ester.

5. The method of claim [2] *1*, wherein the ether is a $C_1$–$C_6$ ether.

6. The method of claim [2] *1*, wherein said pharmaceutically acceptable salt of a carboxylic acid group is a sodium salt or a potassium salt.

7. The method of claim [2] *1*, wherein the alkyl groups are $C_1$–$C_6$ alkyl groups and the alkoxy group is a $C_1$–$C_6$ alkoxy group.

8. The method of claim [2] *1*, wherein said inhibitor of the protein tyrosine kinase pathway is genistein.

* * * * *